US007645396B2

(12) United States Patent
Oda

(10) Patent No.: US 7,645,396 B2
(45) Date of Patent: Jan. 12, 2010

(54) 1,2-BIS(3-METHYLPHENOXY)ETHANE COMPOSITION AND THERMAL RECORDING MEDIA MADE BY USING THE SAME

(75) Inventor: Shigeru Oda, Osaka (JP)

(73) Assignee: Sanko Co., Ltd., Kurume-shi (JP)

( * ) Notice: Subject to any disclaimer, the term of this patent is extended or adjusted under 35 U.S.C. 154(b) by 0 days.

(21) Appl. No.: 12/397,814

(22) Filed: Mar. 4, 2009

(65) Prior Publication Data

US 2009/0166594 A1 Jul. 2, 2009

Related U.S. Application Data

(63) Continuation of application No. 10/545,811, filed as application No. PCT/JP2004/001613 on Feb. 16, 2004, now Pat. No. 7,566,682.

(30) Foreign Application Priority Data

Feb. 18, 2003 (JP) ............................ 2003-039771
Mar. 26, 2003 (JP) ............................ 2003-084413

(51) Int. Cl.
*C09K 3/00* (2006.01)
*B41M 5/20* (2006.01)
*C07C 15/067* (2006.01)

(52) U.S. Cl. ................... 252/182.11; 503/209; 585/446

(58) Field of Classification Search ............ 252/182.11, 252/183.11; 503/209; 585/446
See application file for complete search history.

(56) References Cited

U.S. PATENT DOCUMENTS 4,531,140 A 7/1985 Suzuki et al.
4,731,354 A * 3/1988 Taniguchi et al. ........... 503/209

FOREIGN PATENT DOCUMENTS

| | | |
|---|---|---|
| JP | 62-48587 | 3/1987 |
| JP | 62-263135 | 11/1987 |
| JP | 7-10790 | 1/1995 |
| JP | 8-39937 | 2/1996 |
| JP | 9-207440 | 8/1997 |
| JP | 9-207441 | 8/1997 |
| JP | 2003-252816 | 9/2003 |

* cited by examiner

*Primary Examiner*—James Seidleck
*Assistant Examiner*—Aaron Greso
(74) *Attorney, Agent, or Firm*—Oblon, Spivak, McClelland, Maier & Neustadt, L.L.P.

(57) ABSTRACT

In a thermal recording medium including a basic chromogenic dye, a developer and a sensitizer, a composition for a thermal recording medium which composition contains 50 ppm to 5.0 mass % of 1-(3-methylphenoxy)-2-(4-methylphenoxy)ethane and/or 1,2-bis(4-methylphenoxy)ethane in 1,2-bis(3-methylphenoxy)ethane is used as said sensitizer, whereby the 1,2-bis(3-methylphenoxy)ethane compound is remarkably improved in milling property in the preparation of the above sensitizer, and a thermal recording medium is provided without impairing the colorability, etc., such as thermal colorability.

8 Claims, No Drawings

1,2-BIS(3-METHYLPHENOXY)ETHANE COMPOSITION AND THERMAL RECORDING MEDIA MADE BY USING THE SAME

TECHNICAL FIELD

The present invention relates to a thermal recording medium (thermal recording material) using a thermal coloring reaction of a colorless or light-colored basic chromogenic dye precursor, a developer, a sensitizer, etc., and more specifically, it relates to a thermal recording medium using 1,2-bis(3-methylphenoxy)ethane composition as a sensitizer.

TECHNICAL BACKGROUND

A thermal recording medium, using a thermal coloring reaction of a substantially colorless or light-colored basic chromogenic dye precursor, a developer for causing it to color, a sensitizer, etc., is, as a simple and low priced recording system, widely used in the fields of a thermal facsimile, a thermal printer, a thermal label, and the like. In the above thermal recording media, essentially, a sensitizer is incorporated into a recording layer for improving its thermal colorability. However, thermal colorability and background fogging are often contradictory to each other. In a medium, the more improved in the thermal colorability, the more background fogging is liable to occur. On the other hand, when the more attempt is made to suppress the background fogging, the more deteriorated its colorability is. There is, therefore, strongly demanded to provide a sensitizer that improves both of these two properties in a thermal recording medium.

For complying with the above fundamental demand, a thermal recording medium, using a 1,2-bis(3-methylphenoxy)ethane compound as a sensitizer, has an established reputation as being excellently balanced between the above thermal colorability and background fogging as is described in Japanese Patent No. 1804948. And the above compound is, and has been, widely produced, sold and used for a very long period of time as a typical sensitizer. Basically, a sensitizer is prepared in the form of a coating liquid containing the sensitizer by milling and dispersing the sensitizer in an aqueous medium containing basic components such as a surfactant, an antifoaming agent, a dispersing agent, etc., with a milling apparatus using a milling medium such as a ball mill, a sand mill, or the like, until it generally has a particle diameter of 5 μm or less, preferably 1.5 μm or less.

Generally, 1,2-bis(3-methylphenoxy)ethane is synthesized from 3-methylphenol and 1,2-dihalogenoethane or the like as raw materials and then purified by recrystallization. In a purified state, it is provided in the form of particles most of which have a particle diameter of 50 to 700 μm, and for incorporating it into the above coating liquid, milling thereof is essential.

That is, it is required to mill 1,2-bis(3-methylphenoxy)ethane compound (to be sometimes referred to as "phenoxyethane compound" hereinafter) in an aqueous medium containing components such as a surfactant, an antifoaming agent, a dispersing agent, etc., until it generally comes to have a particle diameter of 5 μm or less, preferably 1.5 μm or less, more preferably 1 μm or less (the particle diameter here and hereinafter refers to an average particle diameter). However, the above phenoxyethane compound is, in principle, a compound that is very hard to mill, and the step of milling the same takes a considerably long time, which is a great bottleneck in the step of producing a thermal recording medium such as a thermal recording paper, or the like, and has been a serious problem to be solved.

It is an object of the present invention to remarkably improve the milling property of the 1,2-bis(3-methylphenoxy)ethane compound excellent in basic performances such as thermal colorability as a sensitizer without impairing the above colorability, and to provide a thermal recording medium using the same as a sensitizer.

The present inventors have made diligent studies for improving the milling of 1,2-bis(3-methylphenoxy)ethane, and as a result have found that the milling property thereof is remarkably improved by preparing a specific composition having a specific content of a specific compound. Further, it has been surprisingly found that a thermal recording medium using such a 1,2-bis(3-methylphenoxy)ethane composition as a sensitizer is not degraded in colorability but is rather unexpectedly improved in colorability. The present invention has been accordingly made on the basis of the above findings.

DISCLOSURE OF THE INVENTION

The present invention has been made from the above viewpoint, and according to the present invention, there is provided the following invention.

1. A sensitizer composition for a thermal recording medium, which contains 1,2-bis(3-methylphenoxy)ethane as a main component, said 1,2-bis(3-methylphenoxy)ethane containing 50 ppm to 5.0 mass % of 1-(3-methylphenoxy)-2-(4-methylphenoxy)ethane and/or 1,2-bis(4-methylphenoxy)ethane.

2. The sensitizer composition for a thermal recording medium as recited in the above 1, wherein said 1,2-bis(3-methylphenoxy)ethane contains 500 ppm to 2.0 mass % of 1-(3-methylphenoxy)-2-(4-methylphenoxy)ethane and/or 1,2-bis(4-methylphenoxy)ethane.

3. A thermal recording medium comprising a substrate and a thermal recording layer formed on the substrate, the thermal recording layer containing at least a basic chromogenic dye precursor and a developer, wherein said recording layer contains the composition recited in the above 1 or 2 as a sensitizer.

4. A thermal recording medium of the above 3, wherein the thermal recording layer contains, as said basic chromogenic dye precursor, at least one member selected from the group consisting of 3-N,N-dibutylamino-6-methyl-7-anilinofluorane, 3-N,N-diethylamino-6-methyl-7-anilinofluorane, 3-(N-isoamyl-N-ethyl)amino-6-methyl-7-anilinofluorane, 3-(N-isopentyl-N-ethyl)amino-6-methyl-7-anilinofluorane, 3-(N-cyclohexyl-N-methyl)amino-6-methyl-7-anilinofluorane, 3-N,N-diethyl-6-chloro-7-anilinofluorane and 3,3-bis(p-dimethylaminophenyl)-6-dimethylaminophthalide.

5. The thermal recording medium of the above 3 or 4, wherein the thermal recording layer contains, as said developer, at least one member selected from the group consisting of 2,2-bis(4-hydroxyphenyl)propane, 2,2-bis(4-hydroxyphenyl)-5-methylpentane, 4-hydroxy-4'-isopropoxy-diphenyl sulfone, 4,4'-dihydroxy-diphenyl sulfone, 2,2-dimethyl-1,3-bis(4-hydroxybenzoyloxy)propane, 2,4'-dihydroxydiphenylsulfone, 3,3'-diallyl-4,4'-dihydroxydiphenyl sulfone, 4-hydroxybenzenesulfone anilide, 2,4-bis(phenylsulfonyl)

phenol, 4,4'-bis(p-toluenesulfonylaminocarbonylamino)-diphenylmethane and 4,4'-[oxybis(ethyleneoxy-p-phenylenesulfonyl)]diphenol.

PREFERRED EMBODIMENTS OF THE INVENTION

The present invention will be explained in detail hereinafter.

The composition for a thermal recording medium, more specifically, the sensitizer composition for a thermal recording medium, provided by the present invention, is a composition for a thermal recording medium, which is prepared by incorporating 50 ppm to 5.0 mass %, preferably 500 ppm to 2.0 mass %, of 1-(3-methylphenoxy)-2-(4-methylphenoxy) ethane and/or 1,2-bis(4-methylphenoxy)ethane into 1,2-bis (3-methylphenoxy)ethane.

(Preparation of Composition of the Invention)

The above composition (to be sometimes referred to as "1,2-bis(3-methylphenoxy)ethane composition", "composition of the present invention" or "sensitizer composition of the present invention" hereinafter) can be obtained by adjusting the composition of raw materials as required when the 1,2-bis(3-methylphenoxy)ethane is synthesized, or can be also obtained by separately preparing 1,2-bis(3-methylphenoxy)ethane, 1-(3-methylphenoxy)-2-(4-methylphenoxy) ethane and 1,2-bis(4-methylphenoxy)ethane, which are components for the above composition, and mixing these. For example, the following methods can be applied.

(a) A method in which 4-methylphenol is incorporated into, or added to, 3-methylphenol that is a main raw material for synthesis of 1,2-bis(3-methylphenoxy)ethane, such that an amount corresponding to the content defined in the present invention is attained, and the resultant mixture is reacted with 1,2-dihalogenoethane such as 1,2-dibromoethane or 1,2-dichloroethane, or the like. In this manner, 1-(3-methylphenoxy)-2-(4-methylphenoxy)ethane and/or 1,2-bis(4-methylphenoxy)ethane are/is formed in 1,2-bis(3-methylphenoxy)ethane that is a main product, to obtain a composition having a desired content thereof. According to this method, the composition of the present invention can be prepared directly, in the course of synthesis.

(b) There can be also employed a method in which 1,2-bis (3-methylphenoxy)ethane, 1-(3-methylphenoxy)-2-(4-methylphenoxy)ethane and 1,2-bis(4-methylphenoxy)ethane are separately prepared in advance, these are mixed, and the mixture is heat-melted and then cooled to crystallize. The above melting and crystallization method provides a more homogeneous composition.

(c) There can also be employed a method in which 1,2-bis (3-methylphenoxy)ethane, 1-(3-methylphenoxy)-2-(4-methylphenoxy)ethane and 1,2-bis(4-methylphenoxy)ethane, prepared in advance, are mixed when subjected to milling, and milled mechanically, to obtain the above composition.

Of the above methods, a suitable method can be employed depending upon an intended composition and the like, and these methods can also be combined as required. The above methods are, however, only typical ones, shown as examples, and the employable preparation methods shall not be limited thereto.

(Contents of Composition of the Invention)

The composition of the present invention is a composition prepared by incorporating 50 ppm to 5.0 mass %, preferably 500 ppm to 2.0 mass % of 1-(3-methylphenoxy)-2-(4-methylphenoxy)ethane and/or 1,2-bis(4-methylphenoxy)ethane into 1,2-bis(3-methylphenoxy)ethane (When the composition contains both 1-(3-methylphenoxy)-2-(4-methylphenoxy)ethane and 1,2-bis(4-methylphenoxy)ethane, the above content refers to the total content thereof). When the content in the above composition is small or less than 50 ppm, the effect on improvement in the milling property, intended in the present invention, is substantially not produced. Further, when the content is too large or exceeds 5.0 mass %, not only the milling property is rather degraded, but also the background fogging of a thermal recording medium at a high temperature is no longer negligible, when the above composition is used as a sensitizer.

The sensitizer of the present invention is suitably used as a sensitizer for a thermal recording medium, and the thermal recording medium may be further improved in sensitivity by using other one or two or more sensitizers in combination therewith. The above sensitizer(s) to be used in combination can be selected from known sensitizers such as diphenyl sulfone, 1,2-bis(phenoxy)ethane, β-naphthyl benzyl ether, dibenzyl oxalate, di-p-methylbenzyl oxalate, p-chlorobenzyl oxalate, stearic acid amide, ethylenebisstearic acid amide, p-benzylbipheny, m-terphenyl, p-biphenyl-p-tolyl ether, and the like.

(Basic Chromogenic Dye Precursor)

The colorless or light-colored basic chromogenic dye precursor (to be sometimes simply referred to as "basic chromogenic dye" or "dye" hereinafter) for use in the thermal recording medium of the present invention is not specially limited, and it can be selected from conventionally known compounds such as a fluorane compound, an indolyl phthalide compound, a divinyl phthalide compound, a pyridine compound, a spiro compound, a fluorene compound, a triarylmethane compound, a diarylmethane compound, and the like. For example, the following compounds are preferred;

Fluorane compounds such as 3-N,N-butylamino-6-methyl-7-anilinofluorane, 3-N,N-diethylamino-6-methyl-7-anilinofluorane, 3-pyridino-6-methyl-7-anilinofluorane, 3-morpholino-6-methyl-7-anilinofluorane, 3-dimethylamino-6-methyl-7-anilinofluorane, 3-diethylamino-6-methyl-7-anilinofluorane, 3-di-n-butylamino-6-methyl-7-anilinofluorane, 3-di-n-pentylamino-6-methyl-7-anilinofluorane, 3-di-n-octylamino-6-methyl-7-anilinofluorane, 3-(N-n-propyl-N-methyl)amino-6-methyl-7-anilinofluorane, 3-(N-n-butyl-N-methyl)amino-6-methyl-7-anilinofluorane, 3-(N-n-butyl-N-ethyl)amino-6-methyl-7-anilinofluorane, 3-(N-isoamyl-N-ethyl)amino-6-methyl-7-anilinofluorane, 3-(N-isobutyl-N-methyl)amino-6-methyl-7-anilinofluorane, 3-(N-isobutyl-N-ethyl)amino-6-methyl-7-anilinofluorane, 3-(N-n-pentyl-N-ethyl)amino-6-methyl-7-anilinofluorane, 3-(N-isopentyl-N-ethyl)amino-6-methyl-7-anilinofluorane, 3-(N-n-hexyl-N-ethyl)amino-6-methyl-7-anilinofluorane, 3-(N-n-octyl-N-ethyl)amino-6-methyl-7-anilinofluorane, 3-(N-cyclopentyl-N-ethyl)amino-6-methyl-7-anilinofluorane, 3-(N-cyclohexyl-N-methyl)amino-6-methyl-7-anilinofluorane, 3-(N-cyclohexyl-N-n-propyl)amino-6-methyl-7-anilinofluorane, 3-(N-cyclohexyl-N-n-butyl)amino-6-methyl-7-anilinofluorane, 3-(N-cyclohexyl-N-n-hexyl) amino-6-methyl-7-anilinofluorane, 3-(N-cyclohexyl-N-n-octyl)amino-6-methyl-7-anilinofluorane, 3-N,N-diethyl-6-chloro-7-anilinofluorane, 3-N-(2'-methoxyethyl)-N-isobutylamino-6-methyl-7-anilinofluorane, 3-N-(2'-ethoxyethyl)-N-ethylamino-6-methyl-7-anilinofluorane, 3-N-(3'-methoxypropyl)-N-methylamino-6-methyl-7-anilinofluorane, 3-N-(3'-ethoxypropyl)-N-methylamino-6-methyl-7-anilinofluorane, 3-N-(3'-ethoxypropyl)-N-ethylamino-6-methyl-7-anilinofluorane, 3-N-(2'-tetrahydrofuryl)-N-ethylamino-6-methyl-7-anilinofluorane, 3-N-(4'-methylphenyl)-N-ethylamino-6-methyl-7-anilinofluorane, 3-pyrrolidino-6-methyl-7-anilinofluorane, 3-morpholino-6-methyl-7-anilinofluorane, 3-dimethylamino-6-methyl-7-anilinofluorane, 3-diethylamino-6-methyl-7-anilinofluorane, 3-di-n-butylamino-6-methyl-7-anilinofluorane, 3-di-n-pentylamino-6-methyl-7-anilinofluorane, 3-di-n-octylamino-6-methyl-7-anilinofluorane, 3-N-n-propyl-N-methylamino-6-methyl-7-anilinofluorane, 3-N-n-butyl-N-methylamino-6-methyl-7-anilinofluorane, 3-N-n-butyl-N-ethylamino-6-methyl-7-anilinofluorane, 3-N-isobutyl-N-methylamino-6-methyl-7-anilinofluorane, 3-N-isobutyl-N-ethylamino-6-methyl-7-anilinofluorane, 3-N-n-pentyl-N-ethylamino-6-methyl-7-anilinofluorane, 3-N-isopentyl-N-ethylamino-6-methyl-7-anilinofluorane, 3-N-n-hexyl-N-ethylamino-6-methyl-7-anilinofluorane, 3-N-n-octyl-N-ethylamino-6-methyl-7-anilinofluorane, 3-N-cyclopentyl-N-ethylamino-6-methyl-7-anilinofluorane, 3-N-cyclohexyl-N-methylamino-6-methyl-7-anilinofluorane, 3-N-cyclohexyl-N-n-propylamino-6-methyl-7-anilinofluorane, 3-N-cyclohexyl-N-n-butylamino-6-methyl-7-anilinofluorane, 3-N-cyclohexyl-N-n-hexylamino-6-methyl-7-anilinofluorane, 3-N-cyclohexyl-N-n-octylamino-6-methyl-7-anilinofluorane, 3-N-(2'-methoxyethyl)-N-isobutylamino-6-methyl-7-anilinofluorane, 3-N-(2'-ethoxyethyl)-N-ethylamino-6-methyl-7-anilinofluorane, 3-N-(3'-methoxypropyl)-N-methylamino-6-methyl-7-anilinofluorane, 3-N-(3'-ethoxypropyl)-N-methylamino-6-methyl-7-anilinofluorane, 3-N-(3'-ethoxypropyl)-N-ethylamino-6-methyl-7-anilinofluorane, 3-N-(2'-tetrahydrofurfuryl)-N-ethylamino-6-methyl-7-anilinofluorane, 3-N-(4'-methylphenyl)-N-ethylamino-6-methyl-7-anilinofluorane, 3,6-dimethoxyfluorane, 3-dimethylamino-7-methoxyfluorane, 3-diethylamino-7-methoxyfluorane, 3-diethylamino-7-methylfluorane, 3-N-cyclohexyl-N-n-butylamino-7-methylfluorane, 3-N-ethyl-N-isopentylamino-7-methylfluorane, 3-diethylamino-7-chlorofluorane, 3-diethylamino-6-methyl-7-chlorofluorane, 3-diethylamino-6,7-dimethylfluorane, 3,6-bis(diphenylamino)fluorane, 3-diethylamino-7-dibenzylaminofluorane, 3-di-n-butylamino-7-dibenzylaminofluorane, 3-diethylamino-7-n-octylaminofluorane, 3-diethylamino-7-anilinofluorane, 3-N-ethyl-N-isopentylamino-7-anilinofluorane, etc.;

Indolyl phthalide compounds such as 3,3-bis(p-dimethylaminophenyl)-6-dimethylaminophthalide, 3,3-bis(1,2-dimethylindol-3-yl)-5-dimethylaminophthalide, 3,3-bis(1,2-dimethylindol-3-yl)-6-dimethylaminophthalide, 3,3-bis(2-phenylindol-3-yl)-6-dimethylaminophthalide, 3,3-bis(1-ethyl-2-methylindol-3-yl)phthalide, 3,3-bis(1-octyl-2-methylindol-3-yl)phthalide, 3-(4-dimethylaminophenyl)-3-(1,2-dimethylindol-3-yl)phthalide, 3-(4-dimethylaminophenyl)-3-(2-methylindol-3-yl)phthalide, 3-(2-ethoxy-4-diethylaminophenyl)-3-(1-ethyl-2-methylindol-3-yl)phthalide, 3-(2-ethoxy-4-dibutylaminophenyl)-3-(1-ethyl-2-methylindol-3-yl)phthalide, 3-(2-ethoxy-4-diethylaminophenyl)-3-(1-octyl-2-methylindol-3-yl) phthalide, etc.;

Divinyl phthalide compounds such as 3,3-bis[2,2-bis(4-dimethylaminophenyl)ethenyl]-4,5,6,7-tetrachlorophthalide, 3,3-bis[2,2-bis(4-pyrrolidinophenyl)ethenyl]-4,5,6,7-tetrabromophthalide, 3,3-bis[2-(4-methoxyphenyl)-2-(4-dimethylaminophenyl)ethenyl]-4,5,6,7-tetrachlorophthalide, 3,3-bis[2-(4-methoxyphenyl)-2-(4-pyrrolidinophenyl)ethenyl]-4,5,6,7-tetrachlorophthalide, etc.;

Pyridine compounds such as 3-(2'-ethoxy-4'-diethylaminophenyl)-3-(1'-ethyl-2'-methylindol-3'-yl)-4 or 7-azaphthalide, 3-(2'-ethoxy-4'-diethylaminophenyl)-3-(1'-ethyl-2'-phenylindol-3'-yl)-4 or 7-azaphthalide, 3-(2'-ethoxy-4'-diethylaminophenyl)-3-(1'-octyl-2'-methylindol-3'-yl)-4 or 7-azaphthalide, 3-(2'-hexyloxy-4'-diethylaminophenyl)-3-(1'-ethyl-2'-methylindol-3'-yl)-4 or 7-azaphthalide, 3-(2'-n-butoxy-4'-diethylaminophenyl)-3-(1'-ethyl-2'-phenylindol-3'-yl)-4 or 7-azaphthalide, 3-(2'-methyl-4'-diethylaminophenyl)-3-(1'-ethyl-2'-methylindol-3'-yl)-4 or 7-azaphthalide, 3-(2'-methyl-4'-diethylaminophenyl)-3-(1'-n-octyl-2'-methylindol-3'-yl)-4 or 7-azaphthalide, 3,3-bis(2'-methoxy-4'-diethylaminophenyl)-4 or 7-azaphthalide, 3,3-bis(2'-ethoxy-4'-diethylaminophenyl)-4 or 7-azaphthalide, etc.;

Spiro compounds such as 3-methylspirodinaphthopyran, 3-ethylspirodinaphthopyran, 3-phenylspirodinaphthopyran, 3-benzylspirodinaphthopyran, 3-methylnaphtho-(3'-methoxybenzo)spiropyran, 3-propylspirodibenzopyran, etc.;

Fluorene compounds such as 3,6-bis(diethylamino)fluorene-9-spiro-3'-(6'-dimethylamino)phthalide, 3-diethylamino-6-(N-allyl-N-methylamino)fluorene-9-spiro-3'-(6'-dimethylamino)phthalide, 3,6-bis(diethylamino)-9-spiro [fluorene-9,6'-6'H-chromeno(4,3-b)indole], 3,6-bis (dimethylamino)-3'-methyl-spiro[fluorene-9,6'-6'H-chromeno(4,3-b)indole], 3,6-bis(diethylamino)-3'-methyl-spiro[fluorene-9,6'-6'H-chromeno(4,3-b)indole], etc.;

Triarylmethane compounds such as 3,3-bis(4'-dimethylaminophenyl)-6-dimethylaminophthalide, 3,3-bis(4'-dimethylaminophenyl)phthalide, 3-(4'-dimethylaminophenyl)-3-(4'-diethylaminophenyl)-6-dimethylaminophthalide, 3-(4'-dimethylaminophenyl)-3-(1'-methylpyrrol-3'-yl)-6-dimethylaminophthalide, etc.;

Diarylmethane compounds such as 4,4-bis-dimethylaminobenzhydrin benzyl ether, N-halophenyl leuco auramine, N-2,4,5-trichlorophenyl leuco auramine, etc.

Of these, 3-N,N-dibutylamino-6-methyl-7-anilinofluorane, 3-N,N-diethylamino-6-methyl-7-anilinofluorane, 3-(N-isoamyl-N-ethyl)amino-6-methyl-7-anilinofluorane, 3-(N-isopentyl-N-ethyl)amino-6-methyl-7-anilinofluorane, 3-(N-cyclohexyl-N-methyl)amino-6-methyl-7-anilinofluorane, 3-N,N-diethyl-6-chloro-7-anilinofluorane and 3,3-bis (p-dimethylaminophenyl)-6-dimethylaminophthalide recited in claim 4 are the most preferred basic dyes. These basic chromogenic dyes may be used alone or in combination of two or more members for adjusting a colored image or obtaining a multi-colorable thermal recording medium or some other purposes.

The amount of the dye per 100 parts by mass of the sensitizer is preferably 10 to 500 parts by mass, more preferably 20 to 400 parts by mass, most preferably 30 to 200 parts by mass. When the above amount is smaller than the above lower limit, no intended colorability can be exhibited. Further, when it is too large, there obtained no further improvement in colorability, rendering it uneconomical.

(Developer)

The developer for use in the thermal recording medium of the present invention includes conventionally known developers such as a phenolic compound, a sulfone-containing compound, an ionic compound, a nitrogen-containing compound, a salicylic acid-containing compound, and the like as compounds that can be used in the present invention.

Above all, preferred are 2,2-bis(4-hydroxyphenyl)propane, 2,2-bis(4-hdyroxyphenyl)-5-methylpentane, 2,2-dimethyl-1,3-bis(4-hydroxybenzoyloxy)propane; 2,2-bis(4-hydroxyphenyl)ethylbenzene; 4-hydroxy-4'-isopropoxydiphenyl sulfone, 4,4'-dihydroxydiphenyl sulfone, 2,4'- dihydroxydiphenyl sulfone, 3,3'-diallyl-4,4'-dihydroxydiphenyl sulfone, 4-hydroxy-4'-allyloxydiphenyl sulfone; 2,4-bis(phenylsulfonyl)phenol, 2,4-bis(phenylsulfonyl)-5-methylphenol, 4,4'-[oxybis(ethyleneoxy-p-phenylenesulfonyl)]diphenol; 1,5-bis(4-hydroxyphenylthio)-3-oxapentane, 1,8-bis(4-hydroxyphenylthio)-3,6-dioxaoctane, 4,4'-bis(p-toluenesulfonylaminocarbonylamino)-diphenylmethane; 4-hydroxybenzenesulfone anilide; 3,5-di-α-methylbenzylsalicylic acid and Zn salt thereof; benzyl 4-hydroxbenzoate, and the like.

Of these, the following compounds, as recited in claim 5, are particularly preferred as a developer. That is, the developer is preferably at least one member selected from the group consisting of 2,2-bis(4-hydroxyphenyl)propane, 2,2-bis(4-hydroxyphenyl)-5-methylpentane, 4-hydroxy-4'-isopropoxy-diphenylsulfone, 4,4'-dihydroxy-diphenyl sulfone, 2,2-dimethyl-1,3-bis(4-hydroxybenzoyloxy)propane, 2,4'-dihydroxydiphenyl sulfone, 3,3'-diallyl-4,4'-dihydroxydiphenyl sulfone, 4-hydroxybenzenesulfone anilide, 2,4-bis(phenylsulfonyl)phenol, 4,4'-bis(p-toluenesulfonylaminocarbonylamino)-diphenylmethane and 4,4'-[oxybis(ethyleneoxy-p-phenylenesulfonyl)]diphenol.

These developers may be used singly or in combination of two or more members. The amount of the developer per 100 parts by mass of the sensitizer is preferably 10 to 500 parts by mass, more preferably 30 to 400 parts by mass, still more preferably 50 to 300 parts by mass.

(Production of Thermal Recording Layer)

The thermal recording layer in the present invention can be produced by any methods known per se, and it is not required to employ any special methods therefor. For example, the basic chromogenic dye, the developer, the sensitizer, a pigment, a metallic soap, wax, etc., are milled and dispersed in an aqueous medium containing a surfactant, an antifoaming agent, a dispersing agent, etc., by means of a ball mill, a sand mill, or the like, until they generally come to have a particle diameter of 5 μm or less, preferably 1.5 μm or less, to prepare a coating liquid.

(Pigment)

The pigment includes those pigments generally used in a thermal recording medium, for example, an inorganic fine powder of any one of kaolin, silica, amorphous silica, calcined kaolin, zinc oxide, calcium carbonate, aluminum hydroxide, magnesium carbonate, titanium oxide, barium sulfate and synthetic aluminum silicate; an organic resin fine powder of any one of a styrene-methacrylate copolymer, a polystyrene resin and a urea-formalin resin, and the like, and these may be used in combination with the above dye.

The amount of the pigment per 100 parts by mass of the basis chromogenic dye is preferably 10 to 2,000 parts by mass, more preferably 20 to 1,000 parts by mass.

(Metallic Soap, Etc.)

Examples of the metallic soap include zinc stearate, calcium stearate, aluminum stearate, and the like.

Further, the wax includes natural waxes such as candelilla wax, rice wax, sumac wax, bees wax, lanolin, montan wax, carnauba wax, ceresin wax, paraffin wax, microcrystalline wax, beef tallow, coconut oil, etc., and further includes derivatives such as polyethylene wax, stearic acid, etc., and Fischer-Tropsch wax, and the like. These may be used singly or in combination.

Examples of the surfactant include sulfosuccinic acid-based alkali metal salt, alkali metal salt of alkylbenzenesulfonic acid, sodium salt of lauryl alcohol sulfuric ester, and the like.

Examples of the antifoaming agent include higher-alcohol-containing, fatty-acid-ester-containing, oil-containing, silicone-containing, polyether-containing, modified-hydrocarbon-oil-containing and paraffin-containing antifoaming agents.

Examples of the dispersing agent include sodium polyacrylate, polyvinyl alcohols (having various saponification degrees, pHs and polymerization degrees), carboxymethyl cellulose, hydroxyethyl cellulose, polyacrylamide, starch, ammonium salt of a styrene-maleic anhydride copolymer, and the like.

As a water resistance improver, further, there may be optionally used 1,1,3-tris(2-methyl-4-hydroxy-5-cyclohexylphenyl)butane, 1,1,3-tris(2-methyl-4-hydroxy-5-tert-butylphenyl)butane, 4-benzyloxy-4'-2,3-propoxy-diphenyl sulfone, and the like.

Further, as a light resistance improver, there include are, for example, benzotriazole-based ultraviolet absorbents such as 2-(2-hydroxy-5-methylphenyl)benzotriazole, 2-(2-hydroxy-3-tert-butyl-5-methylphenyl)-5-chlorobenzotriazole, 2,2-methylenebis[4-(1,1,3,3-tetramethylbutyl)-6-(2H-benzotriazol-2-yl)phenol], microcapsulated 2-(2-hydroxy-3-dodecyl-5-methylphenyl)benzotriazole, and the like.

(Preparation of Thermal Recording Medium)

Conventionally, in the process of producing thermal recording media, the step of preparing a dispersion of raw materials of a dye, a developer, a sensitizer, a pigment, etc., for constituting the thermal recording medium, is generally a rate-determining step, and above all, the step of preparing the dispersion of above sensitizer sometimes takes a long time, for example, as long as 24 hours, causing it a serious problem. According to the present invention, the step of milling the sensitizer is decreased by as much as 40% as will be shown in Examples to be described later. Further, as a milling apparatus, a milling machine having various movable portions such as a ball mill, a sand mill, or the like is used as described above. With a great reduction in the milling time period, therefore, the operation time period of the milling apparatus is also decreased, so that the lifetime of such apparatus is increased to a great extent, which is quite desirable in maintenance of the apparatus.

In the thermal recording medium of the present invention, the thermal recording layer thereof can be formed by a known technology, and the method of forming the same is not specially limited. For example, the recording layer can be formed by applying a coating liquid for the thermal recording layer onto a substrate surface with a proper application apparatus such as an air knife coater, a blade coater, a bar coater, a rod coater, a gravure coater, a curtain coater, a wire bar, or the like and drying the applied coating liquid.

The application amount of the coating liquid is not specifically limited, either. The application amount thereof, as a dry mass, on the substrate surface is preferably in the range of 0.5 to 50.0 $g/m^2$, more preferably 1.0 to 20.0 $g/m^2$. In addition, the substrate is selected from paper, a plastic sheet, a synthetic paper, or the like.

(Undercoat Layer)

In the present invention, further, an undercoat layer may be provided for improving coloring sensitivity. The undercoat layer is formed from a material mainly containing a pigment or organic hollow particles and an adhesive.

The above pigment includes calcined kaolin, magnesium carbonate, amorphous silica, aluminum silicate, magnesium silicate, calcium silicate, calcium carbonate, an urea-formalin resin filler, and the like as are included in the already discussed pigment. Further, the "organic hollow particles" includes homopolymer or copolymer resins of monomers such as vinyl chloride, vinylidene chloride, vinyl acetate, methyl acrylate, ethyl acrylate, methyl methacrylate, acrylonitrile, styrene, and the like.

Further, the adhesive includes water-soluble polymers such as gelatin, casein, starch and a derivative thereof, methyl cellulose, ethyl cellulose, hydroxyethyl cellulose, carboxymethyl cellulose, methoxy cellulose, complete (partial) saponification polyvinyl alcohol, carboxy-modified polyvinyl alcohol, acetoacetyl-modified polyvinyl alcohol, silicon-modified polyvinyl alcohol, an acrylamide-ethyl acrylate copolymer, a styrene-maleic anhydride copolymer, and the like, and hydrophobic polymers such as a styrene-butadiene resin, a styrene-acryl resin, a vinyl acetate resin, an acryl resin, and the like. The formation of the undercoat layer is not specially limited, and it can be formed, for example, like the above-described thermal recording layer.

(Protective Layer)

For improving a shelf life, further, a protective layer may be formed on the thermal recording layer. The protective layer may be formed from an adhesive, a pigment, etc., having film formability, as main components and an ultraviolet absorbent, etc., as optional components.

The adhesive having film formability includes carboxy-modified polyvinyl alcohol, acetoacetyl-modified polyvinyl alcohol, silicon-modified polyvinyl alcohol, diacetone-modified polyvinyl alcohol, and the like. The pigment and the ultraviolet absorbent may be selected from those that are already discussed with regard to the thermal recording layer.

The formation of the above protective layer is not specially limited, either. For example, it can be formed like the above-described thermal recording layer.

In the thermal recording medium, a protective layer may be formed on the reverse surface of the substrate as required, an adhesive layer containing, as a main component, natural rubber, an acrylic-resin-based adhesive or a styrene-isoprene block copolymer and two-package crosslinking acrylic resin adhesive may be formed as required, or each layer after application may be smoothening-treated by super calendering, or the like.

EXAMPLES

The present invention will be explained further in detail hereinafter, while the present invention shall not be limited thereto. In Examples, "%" stands for "mass %" unless otherwise specified. In the present invention, a crystal product or a 1,2-bis(3-methylphenoxy)ethane composition was analyzed by gas chromatography as follows.

(a) Analysis of 1,2-bis(3-methylphenoxy)ethane

Gas chromatograph: Shimadzu GC-14B (FID detector)

Column: Internal diameter 3 mm×1.1 m glass column

Packaging material: Silicone OV-17 3%/uniport HP (60-80 mesh) (supplied by GL Science Corporation)

Column temperature 70→280° C. (temperature elevation rate at 12° C./minute)

(b) Analysis of 1-(3-methylphenoxy)-2-(4-methylphenoxy)ethane and 1,2-bis(4-methylphenoxy) ethane Gas chromatograph: Shimadzu GC-14B (FID detector)

Column: Internal diameter 2.6 mm×2.1 m glass column

Packaging material: KG-02/uniport HP (60-80 mesh) (supplied by GL Science Corporation)

Column temperature: 190° C.

Comparative Example 1

Preparation of 1,2-bis(3-methylphenoxy)ethane composition

A 1 L reactor was charged with 108 g of 3-methylphenol (containing 0.5% of 4-methylphenol) and 100 g of a 48% sodium hydroxide aqueous solution and filled with $N_2$ gas. Then, the mixture was heated to 100° C., and 94 g of 1,2-dibromoethane was charged drop wise into the reactor over 5 hours.

After completion of the drop wise charging, the mixture was aged at 100° C. for 6 hours. After completion of the aging reaction, the reaction solution was allowed to settle to separate it into an aqueous layer and an oil layer. The oil layer was recovered and washed with 50 g of water at 100° C. This washing procedure was repeated twice, then, 1,000 g of methanol was added to the oil layer to form a solution. The solution was filtered, and the filtrate was gradually cooled to 15° C. The formed crystal product was recovered by filtration, and the filtered cake was washed with 100 g of methanol. The resultant crystal product was further purified with 500 g of methanol by recrystallization and dried to give 91 g of a crystal product.

The above crystal product was found to be a 1,2-bis(3-methylphenoxy)ethane composition having a melting point of 98.3° C. and containing 99.99% of 1,2-bis(3-methylphenoxy)ethane, 10 ppm of 1-(3-methylphenoxy)-2-(4-methylphenoxy)ethane and 5 ppm of 1,2-bis(4-methylphenoxy) ethane.

Example 1

Preparation of 1,2-bis(3-methylphenoxy)ethane composition

A 1 L reactor was charged with 108 g of 3-methylphenol (containing 1.0% of 4-methylphenol) and 100 g of a 48% sodium hydroxide aqueous solution and filled with $N_2$ gas. Then, the mixture was heated to 100° C. and allowed to react while 94 g of 1,2-dibromoethane was charged drop wise into the reactor over 5 hours.

After completion of the drop wise charging, the mixture was aged at 100° C. for 6 hours. After the reaction wad completed, the reaction solution was allowed to settle to separate it into an aqueous layer and an oil layer. The oil layer was recovered and washed with 50 g of water at 100° C. This washing procedure was repeated twice, and then 500 g of methanol was added to the oil layer to form a solution. The solution was filtered, and the filtrate was gradually cooled to 15° C. The formed crystal product was recovered by filtration, and the filtered cake was washed with 100 g of methanol. The resultant crystal product was dried, as it was, without carrying out any recrystallization, to give 97 g of a crystal product.

The above crystal product was found to be a composition having a melting point of 98.0° C. and containing 99.45% of 1,2-bis(3-methylphenoxy)ethane, 5,000 ppm of 1-(3-methylphenoxy)-2-(4-methylphenoxy)ethane and 15 ppm of 1,2-bis(4-methylphenoxy)ethane.

Synthesis Example 1

Preparation of 1-(3-methylphenoxy)-2-(4-methylphenoxy)ethane

A 1 L reactor was charged with 108 g of 4-methylphenol (special grade reagent, supplied by Wako Purechemical Ind. Co., Ltd.), 400 g of diethylene glycol dimethyl ether and 62 g of sodium hydroxide, and filled with $N_2$ gas. Then, the mixture was heated to 100° C. to form a solution. The solution was allowed to react at the same temperature while 215 g of 1-bromo-2-(3-methylphenoxy)ethane was charged drop wise into the reactor over 5 hours.

After completion of the drop wise charging, the reaction mixture was aged at 100° C. for 6 hours. After the reaction was completed, the reaction mixture was discharged into 400 g of water. The mixture was cooled to 20° C., and precipitated crystal was recovered by filtration. The filtered cake was washed with 200 g of water, added to 2,000 g of methanol, and the mixture was heated to form a solution, followed by filtration. The resultant filtrate was gradually cooled to 15° C. The formed crystal product was recovered by filtration, and the cake was washed with 200 g of methanol. The resultant crystal product was further purified with 1,000 g of methanol by recrystallization and then dried to give 182 g of 1-(3-methylphenoxy)-2-(4-methylphenoxy)ethane. This product had a melting point of 94° C. with the purity of 99.8%.

Synthesis Example 2

Preparation of 1,2-bis(4-methylphenoxy)ethane

A 1 L reactor was charged with 108 g of 4-methylphenol (special grade reagent, supplied by Wako Purechemical Ind., Co., Ltd.), 600 g of diethylene glycol dimethyl ether, 62 g of potassium hydroxide and filled with $N_2$ gas. Then, the mixture was heated to 100° C. to form a solution. The solution was allowed to react at the same temperature while 94 g of 1,2-dibromoethane was charged drop wise into the reactor over 5 hours.

After completion of the drop wise charging, the reaction mixture was aged at 100° C. for 6 hours. After the reaction was completed, the reaction mixture was discharged into 400 g of water. The mixture was cooled to 20° C., and precipitated crystal was recovered by filtration. The filtered cake was washed with 200 g of water, added to 2,000 g of methanol, and the mixture was heated to form a solution, followed by filtration. The resultant filtrate was gradually cooled to 15° C. The formed crystal product was recovered by filtration, and the cake was washed with 200 g of methanol. The obtained crystal product was further purified with 1,000 g of methanol by recrystallization and then dried to give 200 g of 1,2-bis(4-methylphenoxy)ethane. This product had a melting point of 134° C. and had purity of 99.9%.

Example 2

Preparation of 1,2-bis(3-methylphenoxy)ethane

A 200 mL reactor was charged with 50 g of the 1,2-bis(3-methylphenoxy)ethane composition obtained in Example 1 and 50 mg of the 1-(3-methylphenoxy)-2-(4-methylphenoxy) ethane obtained in Synthesis Example 1, and while the reactor was filled with $N_2$ gas, the mixture was dissolved on heating at 110° C. The resultant solution was discharged into a vat and aged at 70° C. for 10 hours to allow crystallization.

The obtained crystal product was found to be a 1,2-bis(3-methylphenoxy)ethane composition having a melting point of 98.1° C. and containing 99.85% of 1,2-bis(3-methylphenoxy)ethane, 1,000 ppm of 1-(3-methylphenoxy)-2-(4-methylphenoxy)ethane and 5 ppm of 1,2-bis(4-methylphenoxy) ethane.

Example 3

Preparation of 1,2-bis(3-methylphenoxy)ethane composition

A 200 mL reactor was charged with 50 g of the 1,2-bis(3-methylphenoxy)ethane composition obtained in Example 1 and 1.28 g of the 1-(3-methylphenoxy)-2-(4-methylphenoxy) ethane obtained in Synthesis Example 1, and while the reactor was filled with $N_2$ gas, the mixture was dissolved under heat at 110° C. The resultant solution was discharged into a vat and aged at 70° C. for 10 hours to allow crystallization.

The obtained crystal product was found to be a 1,2-bis(3-methylphenoxy)ethane composition having a melting point of 96.3° C. and containing 97.45% of 1,2-bis(3-methylphenoxy)ethane, 2.50% of 1-(3-methylphenoxy)-2-(4-methylphenoxy)ethane and 5 ppm of 1,2-bis(4-methylphenoxy) ethane.

Example 4

Preparation of 1,2-bis(3-methylphenoxy)ethane composition

A 200 mL reactor was charged with 50 g of the 1,2-bis(3-methylphenoxy)ethane composition obtained in Example 1 and 0.25 g of the 1,2-bis(4-methylphenoxy)ethane obtained in Synthesis Example 2, and while the reactor was filled with $N_2$ gas, the mixture was dissolved on heating at 110° C. The resultant solution was discharged into a vat and aged at 70° C. for 10 hours to allow crystallization.

The obtained crystal product was found to be a 1,2-bis(3-methylphenoxy)ethane composition having a melting point of 98.0° C. and containing 99.4% of 1,2-bis(3-methylphenoxy)ethane, 10 ppm of 1-(3-methylphenoxy)-2-(4-methylphenoxy)ethane and 5,000 ppm of 1,2-bis(4-methylphenoxy)ethane.

Example 5

Preparation of 1,2-bis(3-methylphenoxy)ethane composition

A 200 mL reactor was charged with 50 g of the 1,2-bis(3-methylphenoxy)ethane composition obtained in Example 1, 0.25 g of the 1-(3-methylphenoxy)-2-(4-methylphenoxy) ethane obtained in Synthesis Example 1 and 0.25 g of the 1,2-bis(4-methylphenoxy)ethane obtained in Synthesis Example 2, and while the reactor was filled with $N_2$ gas, the mixture was dissolved on heating at 110° C. The resultant solution was discharged into a vat and aged at 70° C. for 10 hours to allow crystallization.

The obtained crystal product was found to be a 1,2-bis(3-methylphenoxy)ethane composition having a melting point of 97.8° C. and containing 98.95% of 1,2-bis(3-methylphenoxy)ethane, 5,000 ppm of 1-(3-methylphenoxy)-2-(4-methylphenoxy)ethane and 5,000 ppm of 1,2-bis(4-methylphenoxy)ethane.

Comparative Example 2

Preparation of 1,2-bis(3-methylphenoxy)ethane composition

A 200 mL reactor was charged with 50 g of the 1,2-bis(3-methylphenoxy)ethane composition obtained in Example 1, 2.8 g of the 1-(3-methylphenoxy)-2-(4-methylphenoxy)ethane obtained in Synthesis Example 1 and 2.8 g of the 1,2-bis(4-methylphenoxy)ethane obtained in Synthesis Example 2, and while the reactor was filled with $N_2$ gas, the mixture was dissolved on heating at 110° C. The resultant solution was discharged into a vat and aged at 70° C. for 10 hours to allow crystallization.

The resultant crystal product was found to be a 1,2-bis(3-methylphenoxy)ethane composition having a melting point of 96.1° C. and containing 89.95% of 1,2-bis(3-methylphenoxy)ethane, 5.0% of 1-(3-methylphenoxy)-2-(4-methylphenoxy)ethane and 5.0% of 1,2-bis(4-methylphenoxy)ethane.

Comparative Example 3

Preparation of 1,2-bis(3-methylphenoxy)ethane composition

A 200 mL reactor was charged with 50 g of the 1,2-bis(3-methylphenoxy)ethane composition obtained in Example 1 and 8.8 g of the 1-(3-methylphenoxy)-2-(4-methylphenoxy)ethane obtained in Synthesis Example 1, and while the reactor was filled with $N_2$ gas, the mixture was dissolved on heating at 110° C. The resultant solution was discharged into a vat and aged at 70° C. for 10 hours to allow crystallization.

The resultant crystal product was found to be a 1,2-bis(3-methylphenoxy)ethane composition (to be referred to as "sample composition" hereinafter) having a melting point of 94.5° C. and containing 84.95% of 1,2-bis(3-methylphenoxy)ethane, 15.0% of 1-(3-methylphenoxy)-2-(4-methylphenoxy)ethane and 4 ppm of 1,2-bis(4-methylphenoxy)ethane.

Example 6

Milling Test/Preparation of Sensitizer Dispersion (1) The 1,2-bis(3-methylphenoxy)ethane composition containing 1,000 ppm of 1-(3-methylphenoxy)-2-(4-methylphenoxy)ethane and 5 ppm of 1,2-bis(4-methylphenoxy)ethane, obtained in Example 2, was subjected to preliminary milling with a milling apparatus (ZM1 type, supplied by Nippon Seiki Seisakusho K.K.) using a woven metal wire (woven metal wire hole: 1.5 mm each side).

Then, the above-milled composition was sieved with a sieve (TESTING SIEVE (opening size 0.85 mm), supplied by IIDA SEISAKUSHO), and a powdery sample composition that passed was used in a milling test.

(2) The milling test was carried out with a triple-blade milling apparatus (TSG4H model, supplied by Igarashi Kikai Seizou K.K.) under the following conditions.

A jacketed pot having a volume of 300 mL was charged with 33.4 g of the above-sieved powdery sample composition, 27.5 g of 5% METOLOSE (dispersing agent, 60SH-03, supplied by Shin-Etsu Chemical Co., Ltd.), 0.2 g of an antifoaming agent (NOPCO1407-K, 5% aqueous solution, supplied by SANNOPCO CORPORATION), 0.4 g of PELEX (PELEX TR, dispersing agent, supplied by Kao Corporation) and 22.0 g of dispersing water. The above powdery composition was caused to well permeate the dispersing water and then allowed to stand for 1 hour.

The above milling apparatus was charged with 200 g of milling medium beads (beads supplied by AS ONE CORPORATION, Product No. BZ-1, bead diameter 1 mm), and milling was initiated with the triple blades at a rotation speed of 1,000 rpm while water at 20 to 25° C. was circulated in the pot jacket.

During the milling step, sample composition was sampled from time to time, and sampled compositions were measured with a particle diameter measuring apparatus (Shimadzu SALD-2000J, supplied by Shimadzu Corporation) with the passage of time. The milling was carried out until an average particle diameter of 1 μm was attained, which took 150 minutes. The thus-obtained composition is a sensitizer dispersion as an end product of the present invention. Table 1 shows the results.

Examples 7-10

Milling Test/Preparation of Sensitizer Dispersion

Sensitizer dispersions were obtained by carrying out experiments in the same manner as in Example 6 except that the 1,2-bis(3-methylphenoxy)ethane composition containing 1,000 ppm of 1-(3-methylphenoxy)-2-(4-methylphenoxy)ethane and 5 ppm of 1,2-bis(4-methylphenoxy)ethane in Example 6 was replaced with 1,2-bis(3-methylphenoxy)ethane compositions obtained in Examples 1, 3, 4 and 5 shown in Table 1. Table 1 shows the results.

Comparative Examples 4-6

Milling Test/Preparation of Sensitizer Dispersion

Sensitizer dispersions were obtained by carrying out experiments in the same manner as in Example 6 except that the 1,2-bis(3-methylphenoxy)ethane composition containing 1,000 ppm of 1-(3-methylphenoxy)-2-(4-methylphenoxy)ethane and 5 ppm of 1,2-bis(4-methylphenoxy)ethane in Example 6 was replaced with 1,2-bis(3-methylphenoxy)ethane compositions obtained in Comparative Examples 1, 2 and 3 shown in Table 1. Table 1 shows the results.

TABLE 1

| | Contents of substance milled (Composition) | | | Time period for |
|---|---|---|---|---|
| | Substance milled | 1-(3-methylphenoxy)-2-(4-methylphenoxy)-ethane | 1,2-bis(4-methylphenoxy)-ethane | milling before an average particle diameter of 1 μm was attained (minutes) |
| Ex. 6 | Ex. 2 | 1000 ppm | 5 ppm | 150 |
| Ex. 7 | Ex. 1 | 5000 ppm | 15 ppm | 140 |
| Ex. 8 | Ex. 3 | 2.50% | 5 ppm | 160 |
| Ex. 9 | Ex. 4 | 10 ppm | 5000 ppm | 150 |
| Ex. 10 | Ex. 5 | 5000 ppm | 5000 ppm | 160 |
| CEx. 4 | CEx. 1 | 10 ppm | 5 ppm | 250 |
| CEx. 5 | CEx. 2 | 5.0% | 5.0% | 240 |
| CEx. 6 | CEx. 3 | 15.0% | 4 ppm | 260 |

Ex. = Example, CEx. = Comparative Example

As is clear from Table 1, it is seen that the compositions according to the present invention have remarkably excellent milling properties over the compositions of Comparative Examples.

That is, conventional milling for preparing an aqueous dispersion of a sensitizer powder for producing thermal recording media takes a time period of approximately 250 minutes even when a small-scale apparatus in Example 1 is used. In the present invention, however, the above time period is decreased to approximately 150 minutes (approximately 40%). As is already discussed, in some actual production apparatuses, the step of preparing an aqueous dispersion of a sensitizer powder takes 24 hours or more in some cases, so that it should be said that the effect of reducing the milling time period in the present invention has a remarkable influences on the entire production process of the thermal recording media.

The mechanism for producing such remarkable improvements attained in milling efficiency when 1-(3-methylphenoxy)-2-(4-methylphenoxy)ethane and 1,2-bis(4-methylphenoxy)ethane having amounts specified in the present invention are incorporated into 1,2-bis(3-methylphenoxy)ethane is not exactly clear. However, it is assumed that when a small amount of a compound having a different structure is incorporated, the crystal structure of the 1,2-bis(3-methylphenoxy)ethane, as a main component, is changed from the state of a very hard or stiff pure substance to a crystal state of a relatively soft mixture.

Further, as a result of remarkable improvements in milling property according to the present invention, it has been found that the above compound can be further milled to give finer particle diameter of less than 1 μm.

Example 11

Preparation of Thermal Recording Medium

The compositions according to the present invention, obtained in Examples 6 to 10, were tested to produce thermal recording media using the compositions as sensitizers.

<Preparation of Coating Liquid for Undercoat Layer>

80 Grams of calcined kaolin (trade name: Ansilex, supplied by Engelhard Corporation), 20 g of calcium carbonate (trade name: Univer 70, supplied by Shiraishi Kogyo K.K.), 140 g of polyvinyl alcohol (trade name: PVA-117, 5% aqueous solution, supplied by Kuraray Co., Ltd.), 15 g of a styrene-butadiene latex (48% emulsion), 2 g of sodium polyacrylate (20% aqueous solution) and 30 g of water were mixed and stirred to give a coating liquid for an undercoat layer.

<Preparation of Coating Liquid for Thermal Recording Layer>

(Preparation of Developer Dispersion)

30 Grams of 4-hydroxy-4'-isopropoxy-diphenyl sulfone was milled in 70 g of a methyl cellulose aqueous solution having a methyl cellulose concentration of 5% with a sand grinder, to prepare an aqueous dispersion of a developer having an average particle diameter of 1.0 μm.

(Preparation of Dye Dispersion)

30 Grams of 3-N,N-dibutylamino-6-methyl-7-anilinofluorane was milled in 70 g of a polyvinyl alcohol (PVA-117) aqueous solution having a polyvinyl alcohol concentration of 5% with a sand grinder, to prepare an aqueous dispersion of a dye having an average particle diameter of 1 μm.

(Preparation of Sensitizer Dispersion)

13.3 Grams of water was added to 40 g of the sensitizer dispersion obtained in Example 6, to prepare a 30% aqueous dispersion.

(Preparation of Pigment Dispersion)

30 Grams of calcium carbonate (Univer 70), 69 g of water and 1.0 g of a 40% sodium hexametaphosphate aqueous solution were stirred with a homogenizer (TK homodisper L type, supplied Tokushu Kika K.K.) at a rotation speed of 5,000 rpm for 5 minutes, to prepare a pigment dispersion.

(Preparation of Coating Liquid for Thermal Recording Layer)

7.2 Grams of the thus-prepared developer dispersion, 3.6 g of the thus-prepared dye dispersion, 7.2 g of the thus-prepared sensitizer dispersion, 7.2 g of the thus-prepared pigment dispersion, 1.8 g of a 30% zinc stearate emulsion (trade name: Hydrin Z-7, supplied by Chukyo Yushi Co., Ltd.) as a lubricant dispersion and 21.6 g of polyvinyl alcohol (PVA-117, 5% aqueous solution, supplied by Kuraray Co., Ltd.) were mixed to obtain a coating liquid for a thermal recording layer.

<Production of Thermal Recording Medium>

The coating liquid for an undercoat layer and the coating liquid for a thermal recording layer were consecutively applied onto one surface of a 64 $g/m^2$ woodfree paper so as to obtain dry application amounts of 10 $g/m^2$ and 3 $g/m^2$, respectively, and each of the applied coating liquids were dried to give a thermal recording medium. In addition, after the undercoat layer and the thermal recording layer were formed, the surfaces thereof were supercalendered to carry out smoothening.

Examples 12-15

Thermal recording media were produced in the same manner as in Example 11 except that the sensitizer in Example 11 was replaced with those shown in Table 2.

Comparative Examples 7-9

Thermal recording media were produced in the same manner as in Example 11 except that the sensitizer in Example 11 was replaced with those shown in Table 2.

TABLE 2

| | Contents of sensitizer (composition) | | |
|---|---|---|---|
| | Milling test No. | 1-(3-methyl-phenoxy)-2-(4-methylphenoxy)-ethane | 1,2-bis(4-methylphenoxy)-ethane |
| Ex. 11 | Ex. 6 | 1000 ppm | 5 ppm |
| Ex. 12 | Ex. 7 | 5000 ppm | 15 ppm |
| Ex. 13 | Ex. 8 | 2.50% | 5 ppm |
| Ex. 14 | Ex. 9 | 10 ppm | 5000 ppm |
| Ex. 15 | Ex. 10 | 5000 ppm | 5000 ppm |
| CEx. 7 | CEx. 4 | 10 ppm | 5 ppm |
| CEx. 8 | CEx. 5 | 5.0% | 5.0% |
| CEx. 9 | CEx. 6 | 15.0% | 4 ppm |

Ex. = Example, CEx. = Comparative Example

<Performance Comparison Test>

Each of the thermal recording papers (thermal recording media) obtained in Examples 11 to 15 and Comparative Examples 7 to 9 was printing-tested with a thermal paper coloring testing apparatus (TH-PMD, supplied by Ohkura Electric Co., Ltd.) using a thermal head (Type KJT-256-8MGFI-ASH, supplied by Kyocera Corporation) 1,653Ω, at a printing voltage of 24 V at a printing frequency (heating time period) of 0.7 msec or 1.4 msec, to test their performances with regard to the following particulars. Table 3 shows the results.

(1) Back Ground and Print Density

Measured with a Macbeth densitometer (RD-948 model, supplied by Macbeth Corporation)

(2) Humidity Durability Test

The above-printed thermal recording papers were left in an atmosphere having a temperature of 45° C. and a humidity of 85% for 24 hours and then measured each for a background fogging and a print density with a Macbeth densitometer. The "background" refers to a whiteness of a portion in a recording paper on which no printing was made.

(3) Heat Resistance Test

Printed thermal recording papers that had been left at 60° C. for 24 hours were measured each for a background fogging and a print density with a Macbeth densitometer in the same manner as in the above measurement.

TABLE 3

| | Initial stage | | | Humidity durability | | Heat resistance | |
|---|---|---|---|---|---|---|---|
| | Back ground | Printing 0.7 msec | Printing 1.4 msec | Back ground | Printing 1.4 msec | Back ground | Printing 1.4 msec |
| Ex. 11 | 0.04 | 0.82 | 1.33 | 0.04 | 1.32 | 0.10 | 1.23 |
| Ex. 12 | 0.04 | 0.83 | 1.34 | 0.04 | 1.33 | 0.10 | 1.24 |
| Ex. 13 | 0.04 | 0.84 | 1.35 | 0.04 | 1.34 | 0.10 | 1.27 |
| Ex. 14 | 0.04 | 0.83 | 1.34 | 0.04 | 1.33 | 0.10 | 1.24 |
| Ex. 15 | 0.04 | 0.83 | 1.34 | 0.04 | 1.33 | 0.10 | 1.26 |
| CEx. 7 | 0.04 | 0.76 | 1.33 | 0.05 | 1.30 | 0.11 | 1.23 |
| CEx. 8 | 0.05 | 0.85 | 1.33 | 0.05 | 1.30 | 0.14 | 1.15 |
| CEx. 9 | 0.05 | 0.86 | 1.33 | 0.06 | 1.29 | 0.18 | 1.17 |

Ex. = Example, CEx. = Comparative Example

In Table 3, it is seen on the basis of initial values that the thermal recording medium of the present invention has little background fogging and has excellent colorability, and it is seen on the basis of humidity durability and heat resistance that the thermal recording medium of the present invention is excellent in retention of a background and a recorded image (printed letters) and these are well-balanced.

Specifically, when almost no amounts of 1-(3-methylphenoxy)-2-(4-methylphenoxy)ethane and 1,2-bis(4-methylphenoxy)ethane are contained (Comparative Example 7), the background fogging is similar to that in Examples of the present invention, but the color density of a print is inferior. It is seen that when the content thereof is greatly outside the range specified in the present invention (Comparative Examples 8 and 6), the thermal recording media thereof are degraded in background fogging or in humidity resistance and heat resistance with regard to a printed color density.

INDUSTRIAL UTILITY

According to the present invention, the milling property of conventional 1,2-bis(3-methylphenoxy)ethane can be remarkably improved without impairing any properties of the compound, as a sensitizer, by introducing a specific composition containing the same compound as a main component, as described above.

Further, it is particularly worth noting that a thermal recording medium using the above 1,2-bis(3-methylphenoxy)ethane composition, as a sensitizer, can stand comparison with, or rather exhibits excellent properties over, a conventional counterpart using a 1,2-bis(3-methylphenoxy)ethane compound per se, as a sensitizer, with regard to media's initial colorability, humidity durability and heat resistance, thereby providing the composition of the present invention with great industrial utility.

The invention claimed is:

1. A method of producing a microparticulated 1,2-bis(3-methylphenoxy)ethane sensitizer composition for a thermal recording medium dispersed in water, which comprises:

preparing a crystalline composition which comprises 1,2-bis(3-methylphenoxy)ethane as a main component and said composition comprising 50 ppm to 5.0 mass % of 1-(3-methylphenoxy)-2-(4-methylphenoxy)ethane and/or 1,2-bis(4-methylphenoxy)ethane as milling improving substances, and milling said crystalline composition with water, thereby producing a microparticulated dispersed 1,2-bis(3-methylphenoxy)ethane sensitizer composition.

2. The method of producing the microparticulated sensitizer composition as defined in claim 1, wherein said crystalline composition is prepared by incorporating or adding 4-methylphenol to 3-methylphenol for synthesis of 1,2-bis(3-methylphenoxy)ethane as a main product, in such as amount corresponding to the designated content of the sensitizer composition, the resultant mixture is reacted with 1,2-dihalogenethane, and the reaction product is crystallized to give said crystalline composition.

3. The method of producing the microparticulated sensitizer composition as defined in claim 1, wherein said crystalline composition is prepared by mixing separately-prepared crystalline 1,2-bis(3-methylphenoxy)ethane, 1-(3-methylphenoxy)-2-(4-methylphenoxy)ethane and/or 1,2-bis(4-methylphenoxy)ethane, in such an amount that corresponds to the designated content of the sensitizer composition, the mixture is heat-melted, and then cooled to crystallize to give said crystalline composition.

4. The method of producing the microparticulated sensitizer composition as defined in claim 1, wherein said crystalline composition is prepared by mixing separately-prepared crystalline 1,2-bis(3-methylphenoxy)ethane, 1-(3-methylphenoxy)-2-(4-methylphenoxy)ethane and/or 1,2-bis(4-methylphenoxy)ethane, in such an amount that corresponds to the designated content of the sensitizer composition when subjected to milling, and being milled mechanically, to give said crystalline composition.

5. The method of producing the microparticulated sensitizer composition as defined in claim 1, wherein said crystalline 1,2-bis(3-methylphenoxy)ethane composition contains 500 ppm to 5.0 mass % of 1-(3-methylphenoxy)-2-(4-methylphenoxy)ethane and/or 1,2-bis(4-methylphenoxy)ethane.

6. The method of producing the microparticulated sensitizer composition as defined in claim 1, wherein said 1,2-bis(3-methylphenoxy)ethane as milled has a particle size of 5.0 μm or less.

7. The method of producing the microparticulated sensitizer composition as defined in claim 1, wherein said 1,2-bis(3-methylphenoxy)ethane as milled has a particle size of 1.5 μm or less.

8. The method of producing the microparticulated sensitizer composition as defined in claim 1, wherein said 1,2-bis(3-methylphenoxy)ethane as milled has a particle size of 1.0 μm or less.

* * * * *